United States Patent
Ballow et al.

(10) Patent No.: US 6,179,813 B1
(45) Date of Patent: Jan. 30, 2001

(54) VASCULAR INFUSION DEVICE

(75) Inventors: Owen A Ballow, Manchester, MI (US); Laurence D. Brenner, Queensbury, NY (US); Mark H. VanDiver, Schaghticoke, NY (US); Gerald A. Zukowsky, Queensbury, NY (US)

(73) Assignee: Scimed Life Systems, Inc., Maple Grove, MN (US)

( * ) Notice: Under 35 U.S.C. 154(b), the term of this patent shall be extended for 0 days.

(21) Appl. No.: 09/066,223

(22) Filed: Apr. 24, 1998

(51) Int. Cl.[7] ............................ A61M 5/178; A61M 5/00; A61M 25/00
(52) U.S. Cl. ........................ 604/164; 604/173; 604/264; 604/523
(58) Field of Search .............................. 604/96, 104, 158, 604/173, 164, 264, 508, 523, 535

(56) References Cited

U.S. PATENT DOCUMENTS

| | | | |
|---|---|---|---|
| 3,670,729 | 6/1972 | Bennett et al. | 128/214.4 |
| 4,149,535 | 4/1979 | Volder | 128/214.4 |
| 4,342,315 | * 8/1982 | Jackson | 128/349 R |
| 4,717,379 | 1/1988 | Ekholmer | 604/43 |
| 4,781,678 | 11/1988 | de Couet et al. | 604/45 |
| 4,968,306 | 11/1990 | Huss et al. | 604/264 |
| 5,021,044 | 6/1991 | Sharkawy | 604/53 |
| 5,147,334 | 9/1992 | Moss | 604/264 |
| 5,178,611 | 1/1993 | Rosenberg | 604/172 |
| 5,207,655 | 5/1993 | Sheridan | 604/247 |
| 5,215,527 | * 6/1993 | Beck et al. | 604/164 |
| 5,250,038 | 10/1993 | Melker et al. | 604/264 |
| 5,324,276 | 6/1994 | Rosenberg | 604/269 |
| 5,354,271 | 10/1994 | Voda | 604/49 |
| 5,395,341 | * 3/1995 | Slater | 604/164 |
| 5,403,291 | 4/1995 | Abrahamson | 604/280 |
| 5,405,334 | 4/1995 | Roth et al. | 604/264 |
| 5,409,463 | 4/1995 | Thomas et al. | 604/167 |
| 5,425,723 | 6/1995 | Wang | 604/280 |
| 5,533,986 | 7/1996 | Mottola et al. | 604/264 |
| 5,626,564 | 5/1997 | Zhan et al. | 604/164 |
| 5,647,859 | 7/1997 | Lampropoulos et al. | 604/264 |
| 5,647,860 | 7/1997 | Roth et al. | 604/264 |
| 5,665,076 | 9/1997 | Roth et al. | 604/264 |
| 5,672,158 | 9/1997 | Okada et al. | 604/164 |
| 5,810,780 | * 9/1998 | Brimhall et al. | 604/167 |

OTHER PUBLICATIONS

New Sheath for Vascular Access and Subcutaneous Drug Administration: Multicenter Clinical Trial for Pain Prevention After Cardiac Catheterization; Lambert, Charles R. et al.; Catheterization and Cardiovascular Diagnosis 40:81–83 (1997).

The Interventional Vascular Access Sheath—The Legacy of Donald T. Desilets, M.D. (1935–1996); Grollman, Jr., Julius H.; Catheterization and Cardiovascular Diagnosis 40:84 (1997).

Side–Hole Sheath; Hideaki Sakai (Yahata Hospital, Kitakyushu, Japan); Medikit Co. and Terumo Co.; Mar. 31, 1998.

* cited by examiner

*Primary Examiner*—Ronald Stright
*Assistant Examiner*—Michael J. Hayes
(74) *Attorney, Agent, or Firm*—Todd P. Messal

(57) ABSTRACT

A vascular access device for infusion of fluids into a patient. The device includes an introducer sheath having one or more side holes and the sheath can be used with a catheter in place through the sheath, with a dilator in place through the sheath, or with the sheath vacant. The device provides for a significant volume of infused fluid to exit the side holes. The side holes allow for the infusion of fluids, such as medications, to be directed to specific patient locations rather than to have the entire volume of infused fluid exit the distal end of the sheath tube.

20 Claims, 6 Drawing Sheets

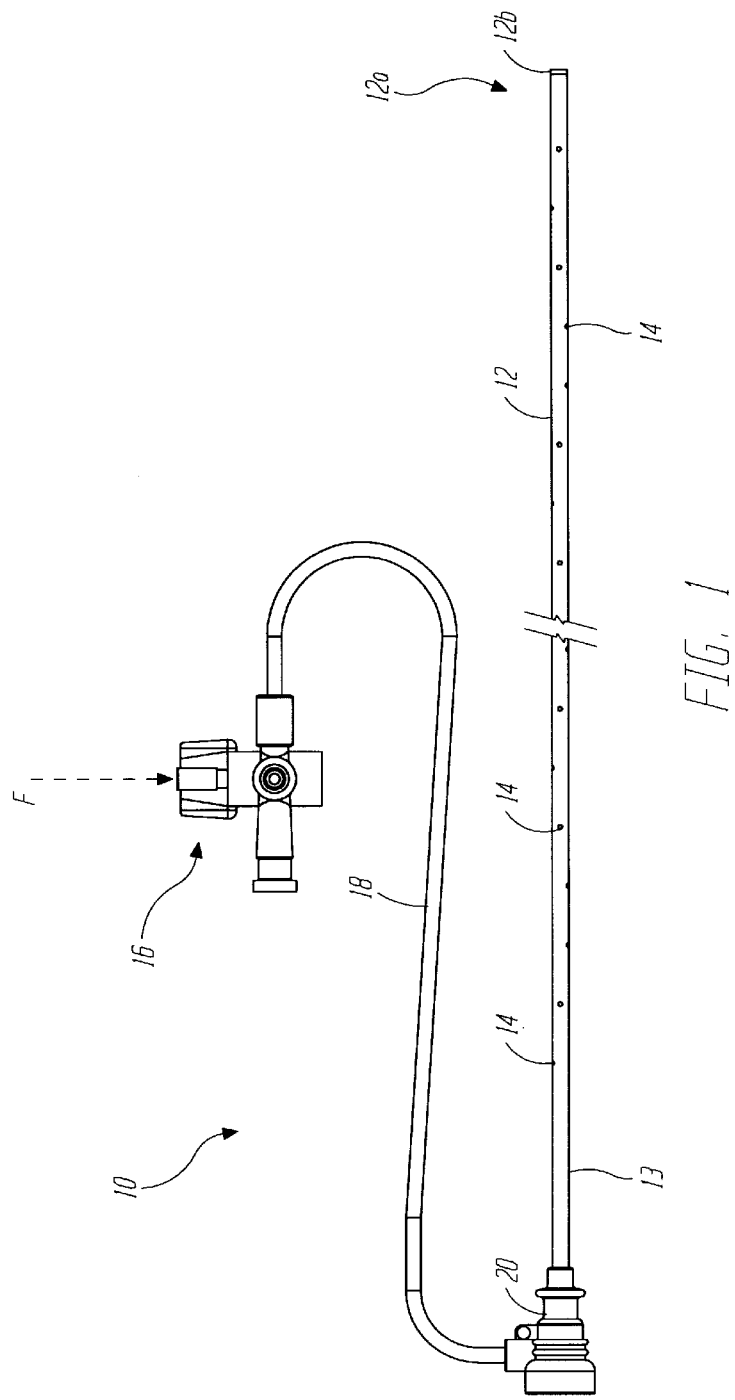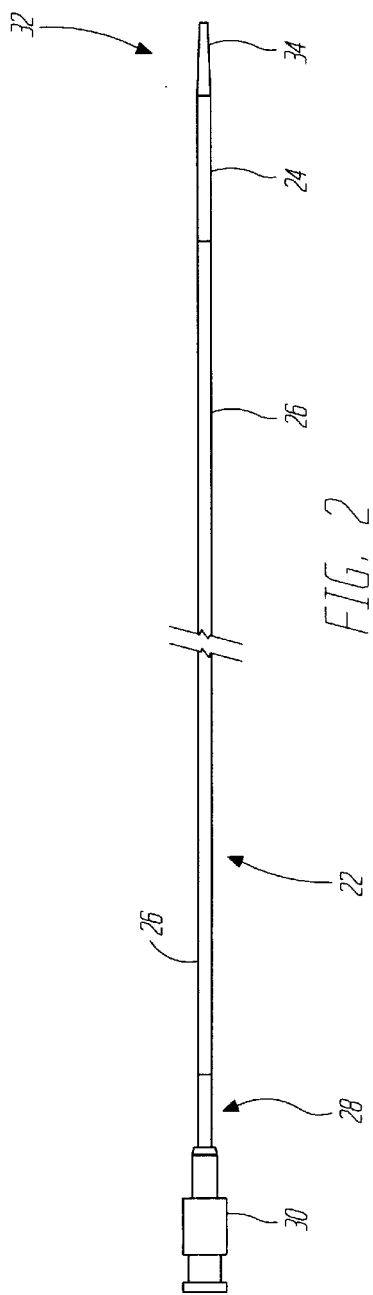

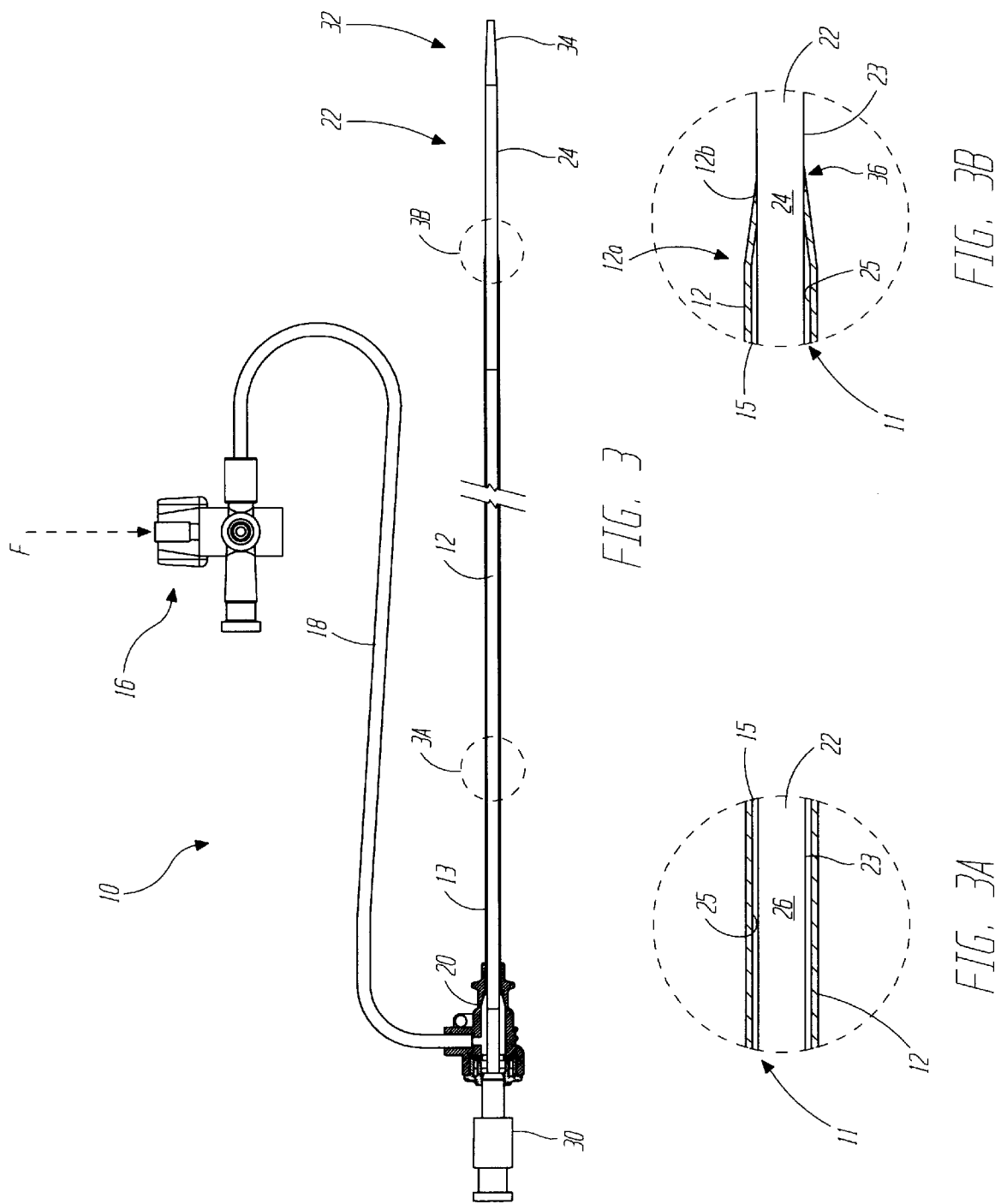

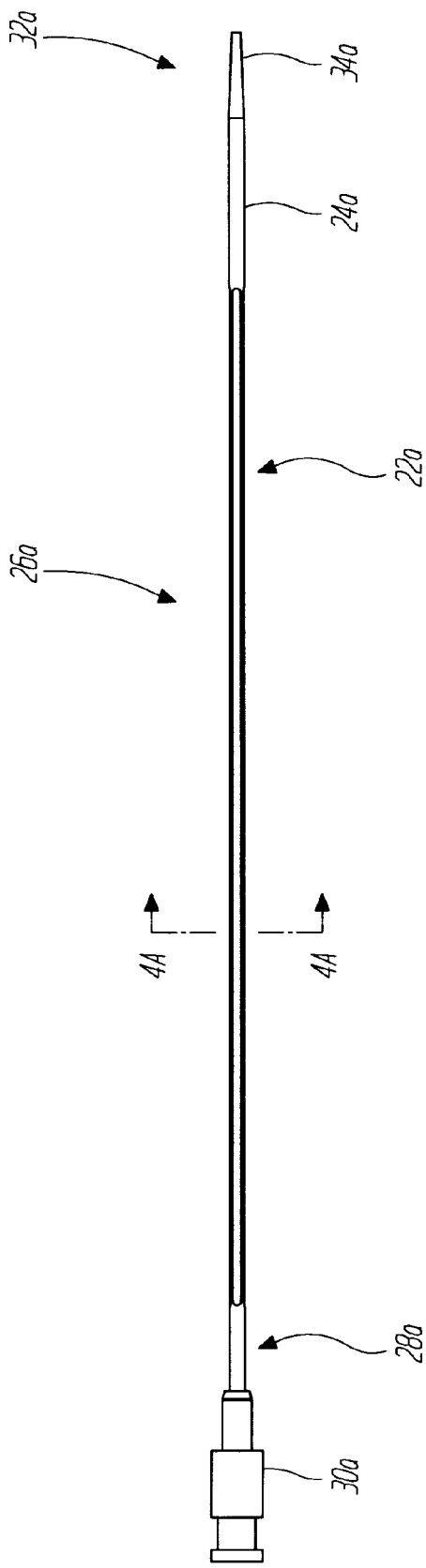
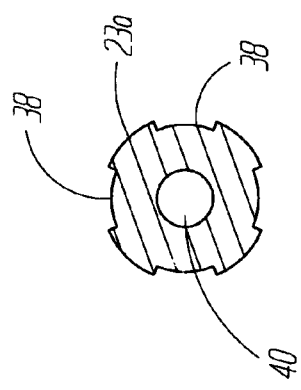
FIG. 4
FIG. 4A

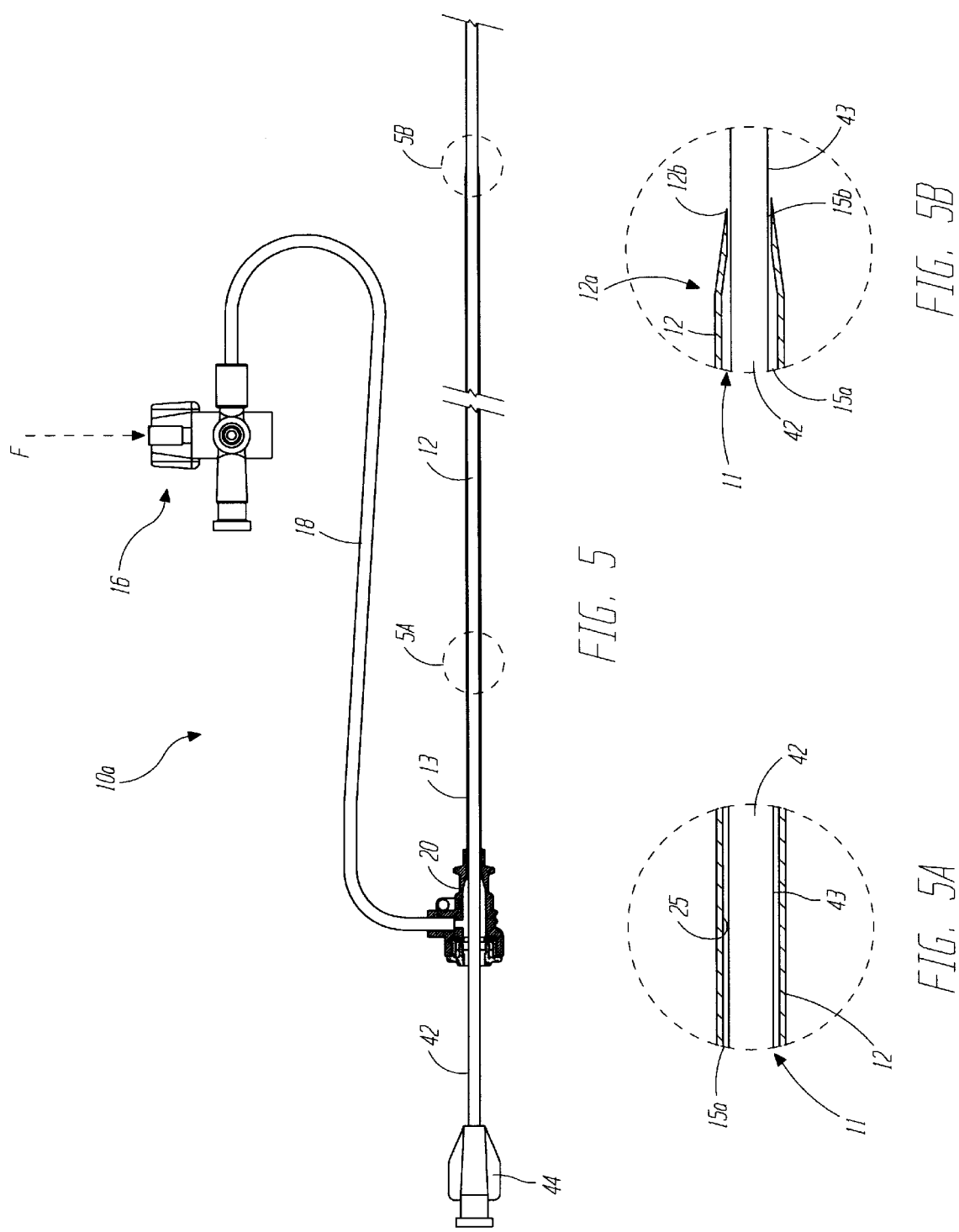

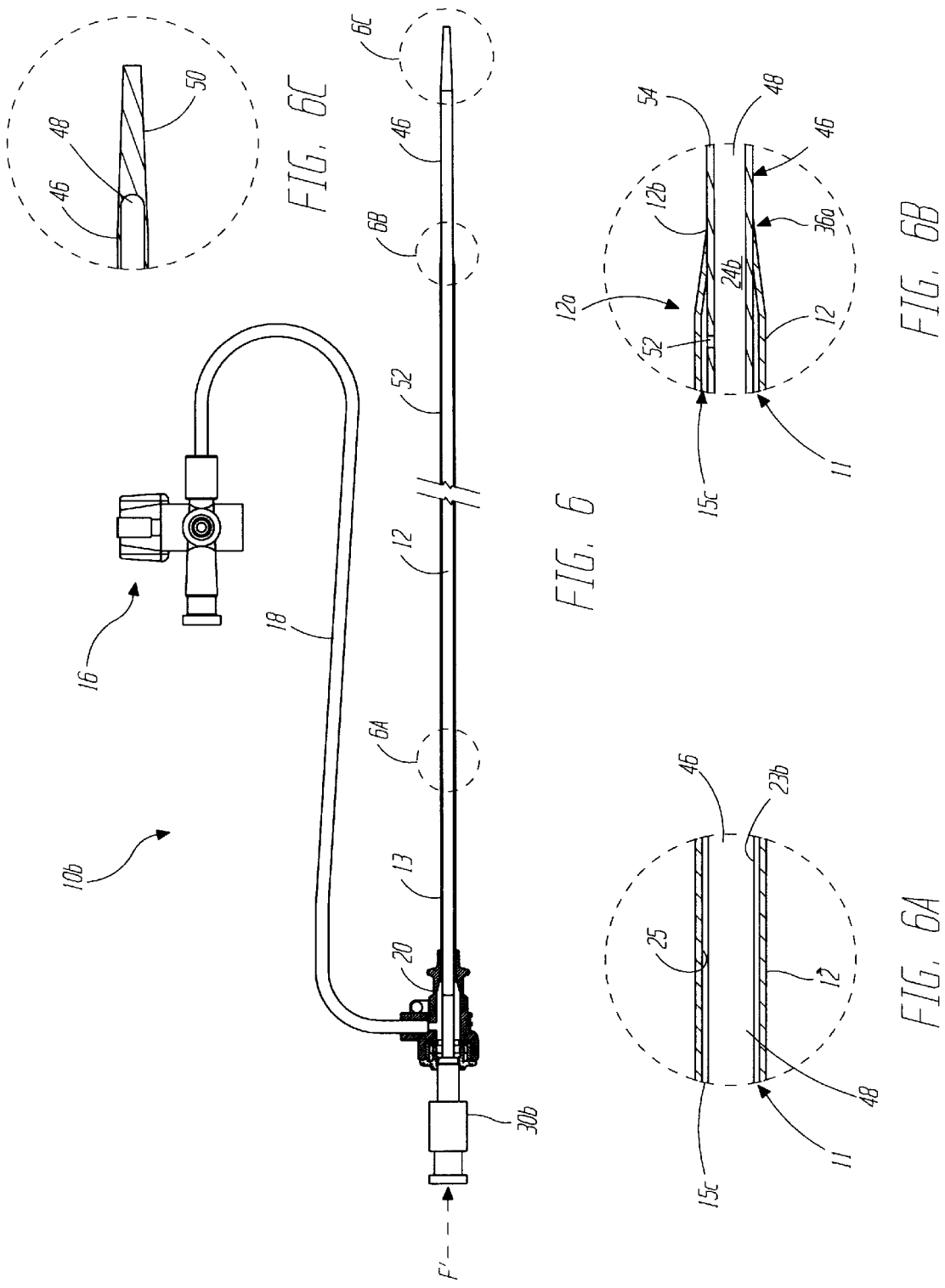

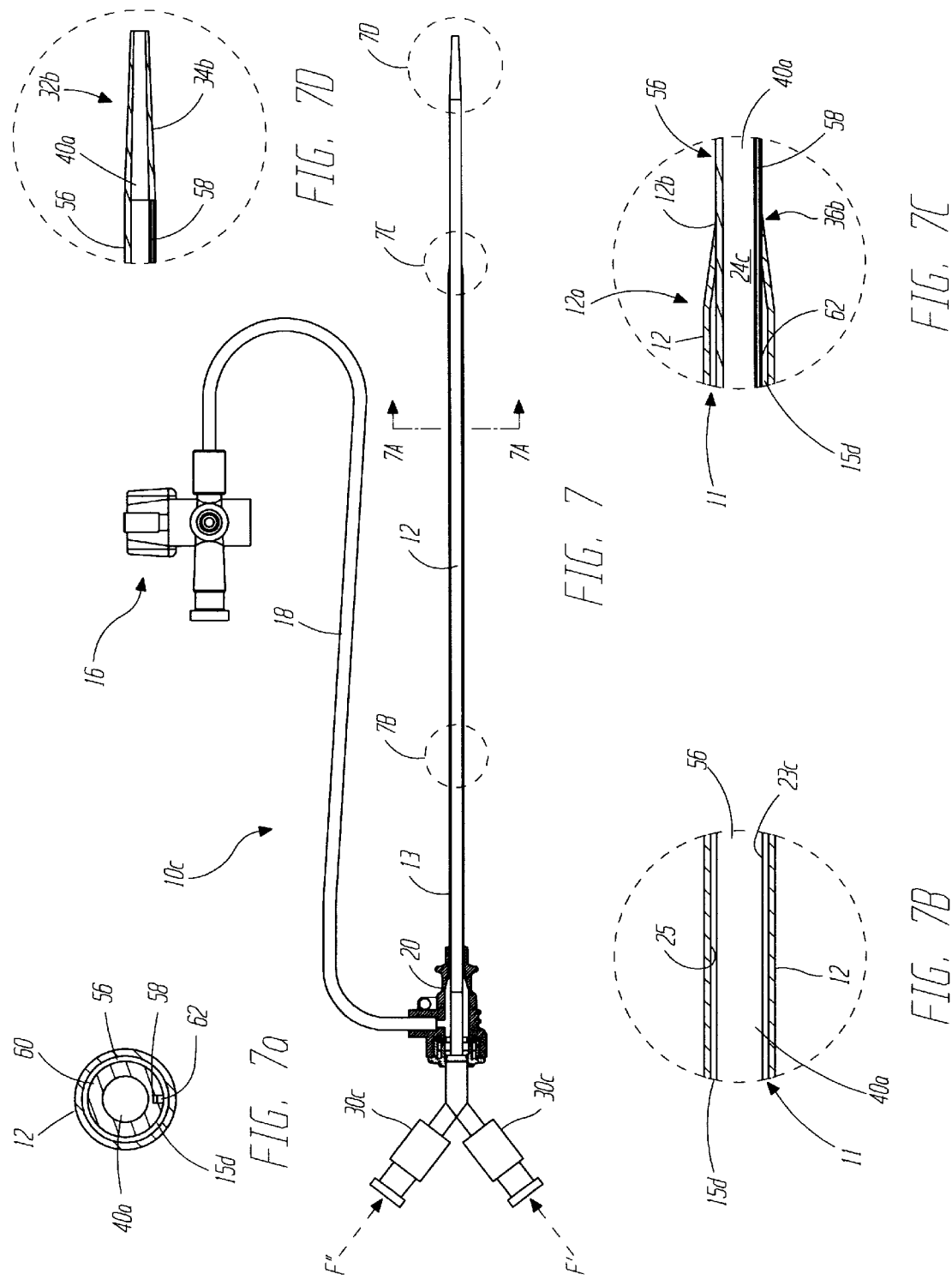

VASCULAR INFUSION DEVICE

BACKGROUND OF THE INVENTION

The present invention relates generally to medical devices suitable for use in delivering fluids to a patient. More particularly, the invention relates to an introducer sheath which will include side holes configured such that the holes appear longitudinally and circumferentially along the sheath tubing to provide an outlet for medications injected into the sidearm of the sheath. The holes will allow medication to be directed to specific locations rather than to have the entire volume of medication exit the distal end of the sheath tube.

The clinical utility of the infusion sheath relates to the ability to infuse medications, specifically medications intended to counteract vasospasm. Vasospasm is a common problem, particularly in the transradial catheterization technique. The result of vasospasm is difficulty in sheath removal and accompanying patient discomfort at the end of a catheterization procedure. To minimize or eliminate vasospasm, physicians will commonly administer a 'cocktail' of medications. An example of such a cocktail would be a mixture of Verapamil, Nitroglycerine, and Xylocaine, Verapamil being an antispasmotic agent. This mixture would be injected through the sideport of the sheath, often prior to withdrawing the sheath, to minimize vasospasm and discomfort. With current sheath designs, the fluid will exit in its entirety out the end of the sheath. With a 21 cm sheath, this presents the potential for the drugs to be significantly distant from where the spasming may be taking place. The tendency of the medications will be to flow in the direction of the blood flow which will be back towards the proximal end of the sheath tubing (for example, flowing from the elbow area back towards an insertion site in the wrist). However, the sheath tubing is large in relation to the radial artery lumen size and therefore may obstruct the medications from getting to the specific portion of the radial artery which is spasming. It is important to note that prior to performing a radial artery procedure, the physician must first ascertain whether the patient has good collateral blood flow into the hand. This is so that if the radial artery is not providing sufficient flow due to sheath obstruction, the ulnar artery can continue to provide sufficient circulation.

The infusion sheath design of the present invention overcomes these clinical problems. By providing infusion ports along a significant portion of the sheath tubing, the drugs can exit the sheath at the point where spasming may be occurring and have a quicker, and perhaps, more effective response. Some prior art teachings disclose side holes or slits which communicate with specifically designated lumens within the wall of the sheath. The present invention allows for a sheath which maintains the critical aspects of being able to have appropriate wall thickness such that insertability and the size of the puncture are not compromised. The design of the sheath and a dilator, which, in some instances, will be used in combination with the sheath, to accommodate this objective is significantly different than other known configurations in sheaths or catheters.

SUMMARY OF THE INVENTION

The present invention is directed toward a vascular device adapted for infusion of fluids into a patient comprising an elongated tubular member having a proximal end, a distal end and a wall extending between the proximal end and the distal end, the wall having an inner surface and an outer surface, at least one lumen extending between the proximal end and the distal end and communicating with the inner surface, with the at least one lumen being adapted to receive a fluid, and one or more apertures disposed in the wall along a length between the proximal end and the distal end for providing fluid communication between the inner surface and the outer surface and adapted for conveying the fluid between the at least one lumen and an environment surrounding the outer surface. The apertures might be disposed circumferentially about the wall, as for example, in a helical pattern, or the apertures might be disposed longitudinally along the wall, as for example, in one or more rows. The apertures may have a diameter in a range of from about 0.025 mm to about 0.600 mm. Preferably, the apertures might have a diameter of about 0.125 mm. The apertures might be spaced from about 1 mm to about 200 mm apart. Preferably, the apertures might be spaced about 10 mm apart. The tubular member might have a length in a range of from about 10 cm to about 25 cm. Further included is a means for delivering the fluid to the lumen.

The invention further embodies a vascular device for infusion of fluids into a patient comprising a first elongated tubular member having a proximal end, a distal end, a first lumen extending therethrough and a first wall having an outer surface and extending between the proximal end and the distal end, a second tubular member having a second wall and being positioned within the lumen to define a space between the first wall and the second wall, the space being adapted to receive a fluid, the second tubular member being sized and configured to create a fluid seal proximate the distal end of the first tubular member, and one or more apertures disposed in the first wall between the proximal end and the distal end for providing fluid communication between the space and an environment surrounding the outer surface of the first wall, wherein fluid introduced into the space exits the device substantially only through the one or more apertures along the length of the outer surface of the first wall. The apertures might be disposed circumferentially about and longitudinally along the first wall. The second tubular member is preferably a dilator which comprises a first portion having a first cross section and a second portion having a second cross section, with the first cross section being greater than the second cross section. The first cross section at a first predetermined location has a cross section being at least equal to the lumen at the first predetermined location. The second cross section at a second predetermined location has a cross section being less than the lumen at the second predetermined location. The dilator might include at least one groove disposed in an outer surface along a length of the dilator. The dilator might further comprise a closed distal end and a second lumen therein communicating with the space, the second lumen being adapted to receive the fluid and delivering the fluid to the space. The second wall of the dilator might comprise one or more second lumens disposed in the second wall communicating with the space, the one or more second lumens being adapted to receive the fluid and delivering the fluid to the space.

The invention still further embodies a vascular device for infusion of fluids into a patient comprising a first elongated tubular member having a proximal end, a distal end and a lumen extending therethrough, a first wall extending between the proximal end and the distal end, with the first tubular member having a through opening at the distal end, a second tubular member having a second wall and being positioned within the lumen to define a space between the first wall and the second wall, the space being adapted to receive a fluid, with a portion of the second member extending through the opening at the distal end of the first tubular member, and one or more apertures disposed in the first wall between the proximal end and the distal end for providing fluid communication between the space and an environment external of the device, wherein a portion of the fluid introduced into the space exits the device through the one or more apertures along the length of the first wall. Preferably the second tubular member is a catheter and the apertures are disposed circumferentially about and longitudinally along the first wall.

In yet another embodiment of the invention embraces a vascular device for infusion of fluids into a patient comprising a first elongated tubular member having a proximal end, a distal end and a lumen extending therethrough, a first wall having an outer surface and extending between the proximal end and the distal end, a second tubular member having a second wall and being positioned within the lumen to define a space between the first wall and the second wall, the space being adapted to receive a fluid, and one or more apertures disposed in the first wall between the proximal end and the distal end for providing fluid communication between the space and an environment surrounding the outer surface of the first wall, wherein fluid introduced into the space exits the device substantially only through the one or more apertures along the length of the outer surface of the first wall. Preferably, the second tubular member is a dilator.

BRIEF DESCRIPTION OF THE DRAWINGS

FIG. 1 is a partial, elevation view of an embodiment of a vascular access device in accordance with the principles of the present invention and illustrating an infusion sheath with side holes for the delivery of fluid into a patient.

FIG. 2 is a partial, elevation view of a dilator adapted for use with the access device of FIG. 1.

FIG. 3 is a partial, sectional view, in elevation, of the device of FIG. 1 with the dilator of FIG. 2 inserted into the infusion sheath.

FIG. 3A is an enlarged sectional view of the area signified by 3A of FIG. 3.

FIG. 3B is an enlarged sectional view of the area signified by 3B of FIG. 3.

FIG. 4 is an elevation view of a modified dilator.

FIG. 4A is an enlarged, cross sectional view of the dilator of FIG. 4 taken along sight line 4A—4A.

FIG. 5 is a partial, sectional view, in elevation, of the device of FIG. 1 with a catheter inserted into the infusion sheath.

FIG. 5A is an enlarged sectional view of the area signified by 5A of FIG. 5.

FIG. 5B is an enlarged sectional view of the area signified by 5B of FIG. 5.

FIG. 6 is a partial, sectional view, in elevation, of the device of FIG. 1 with another modified dilator inserted into the infusion sheath.

FIG. 6A is an enlarged sectional view of the area signified by 6A of FIG. 6.

FIG. 6B is an enlarged sectional view of the area signified by 6B of FIG. 6.

FIG. 6C is an enlarged sectional view of the area signified by 6C of FIG. 6.

FIG. 7 is a partial, sectional view, in elevation, of the device of FIG. 1 with another modified dilator inserted into the infusion sheath.

FIG. 7A is an enlarged, cross sectional view of the device of FIG. 7 taken along sight line 7A—7A.

FIG. 7B is an enlarged sectional view of the area signified by 7B of FIG. 7.

FIG. 7C is an enlarged sectional view of the area signified by 7C of FIG. 7.

FIG. 7D is an enlarged sectional view of the area signified by 7D of FIG. 7.

DETAILED DESCRIPTION OF THE PREFERRED EMBODIMENTS

The description herein presented refers to the accompanying drawings in which like reference numerals refer to like parts throughout the several views. Referring to FIG. 1, in accordance with the principles of the present invention, there is illustrated a partial (shortened), elevation view of a first embodiment of a vascular access device 10. The device 10 includes an infusion sheath 12 with distal end portion 12*a* having a distal end 12*b* and side holes 14 for the delivery of fluid, such as medicaments, into a patient. Sheath 12 has a lumen 11 (not shown in this view but shown in at least FIG. 3). Fluids or medications might be injected, in the direction as indicated by the dashed line with arrow F, by syringe or the like through a stopcock 16 attached to a sidearm 18 at one end and delivered through sidearm 18 to sheath 12 via attachment of sidearm 18 to a hub 20 located at an end of sheath 12. The holes 14 are located such that infusion will be provided along a substantial length of the sheath 12 tubing that is actually in an artery when the artery is being accessed. A gap 13 will exist between the hub 20 and a first hole 14 such that fluid infusion will take place only within a patient's body but generally it will not take place in subcutaneous tissue. The holes 14 are in communication with the main lumen 11 of the sheath.

The side holes 14 of sheath 12 are extremely small. The holes can range from about 0.025 mm to about 0.600 mm in diameter and preferably about 0.125 mm. The holes can be displayed in the sheath wall in a variety of ways, for example, circumferentially, helically, or longitudinally. Hole sizing is important for at least two design aspects. The first is that because of the length of the sheath tubing, typically from about 10 cm to about 25 cm, having larger holes would have the affect of the majority of the fluid exiting the holes proximally located, namely toward hub end 20. The small holes create enough resistance such that it is possible to get very balanced flow out of as many as 17 side holes. The holes might be spaced from about 1 mm to about 200 mm apart and suitably about 10 mm apart. The second key aspect of the size of these holes is that one cannot compromise the strength of the sheath tubing. Sheaths are inherently very thin walled to allow for good insertability and minimal puncture size. By putting holes in such a thin wall tubing, there is a likelihood that the strength of the tubing will be compromised. This weakness can take the form of kinking or buckling of the tubing. The very small holes employed as part of the invention will minimize, and most likely eliminate, this likelihood. The process utilized to create these holes will likely be some means, such as, for example, by drilling or by a laser drilling operation.

A dilator 22 as shown in FIG. 2 would be suitable for use with device 10. The dilator of FIG. 2 has a first portion or segment comprising a first, enlarged section 24, a second portion or segment comprising a second, reduced section 26, a proximal end portion 28 having a hub 30, and a distal end portion 32 having a distal tip 34.

Turning to FIG. 3, there is illustrated device 10 with dilator 22 inserted into lumen 11 of sheath 12. Although holes 14 of sheath 12 are not shown in this view, it should be understood that the holes are present and they are configured and spaced as provided in connection with the description of FIG. 1. Dilator hub 30 coacts with sheath hub 20 to maintain the position of the dilator within the sheath. FIG. 3A is an enlarged sectional view depicting dilator 22 with a portion of reduced section 26 located in sheath 12 and further depicts space 15 created between outer wall surface 23 of dilator 22 and innerwall surface 25 of sheath 12. Section 26 is sized and configured such that it is smaller in cross section than lumen 11 to create space for the passage of fluid. It is the space 15 which receives fluid F directed through the sidearm 18 and passes the fluid through sheath holes 14 (not shown in this view) for delivery of the fluid to the environment surrounding sheath 12. FIG. 3B is an enlarged sectional view depicting distal end portion 12a of sheath 12 and showing enlarged dilator portion 24 forming a seal 36 to create a fluid barrier at the distal end of the sheath. At the location of seal 36, the diameter of enlarged dilator section 24 is at least equal to lumen 11 at the distal end 12b of sheath 12 and may be slightly larger to create a fluid tight friction seal. Substantially all introduced fluid F will exit side holes 14.

It is important to control the flow of medications in this application. Current sheaths do not have infusion side holes and allow for a gap between a catheter inserted through the sheath and the sheath itself. This has the benefit of allowing for pressure monitoring or a slow infusion of fluids. This gap would allow for some amount of the medication to escape out the distal end of the sheath. To prevent this, the aforementioned dilator of the present invention effectively seals off the end of the sheath. This forces the medication to flow out the infusion ports rather than the distal end of the sheath. The outside diameter of a dilator could be ground down in the area where it matches up with the infusion ports but a standard dilator outside diameter could be employed at the sheath tip such that there is a blockage which prevents fluids from flowing out the end. While a likely process to reduce the outside diameter of the dilator will be a grinding operation, others means of allowing for this flow could be employed such as grooves (FIG. 4) extruded into the dilator tubing or any other means by which fluid can be made to flow through or around the dilator and exit the side holes.

Next turning to FIG. 4, there is illustrated a modified dilator 22a suitable for use with device 10 in a manner such as that depicted in FIG. 3. Dilator 22a has a first segment comprising a first section 24a, a second segment of reduced section 26a, a proximal end portion 28a having a hub 30a, and a distal end portion 32a having a distal tip 34a. Second segment 26a includes one or more grooves 38 cut longitudinally therein along outer wall surface 23a of dilator 22a. Section 26a is sized and configured such that it might have essentially the same outer dimension at 23a as that of lumen 11, namely the diameter of section 26a at 23a might essentially be the same as the diameter of lumen 11. It should be understood that grooves 38 would create a space or passageway which would perform the function of space 15 for the passage of fluid. Dilator 22a further includes a lumen 40 which might be a through lumen, that is, it might pass through distal tip 34a or it might terminate prior to distal tip 34a. Depiction of the device in use with device 10 would be similar to the illustration of FIG. 3. A fluid seal would be created at location 36 like that depicted in FIG. 3 and fluid would be delivered as in connection with the illustration of FIG. 3 for passage along grooves 38 for exit through sheath side holes 14.

FIG. 5 illustrates another embodiment 10a of the invention wherein there is shown a partial (shortened) sectional view, in elevation, of device 10 with a catheter 42 having hub 44 inserted into lumen 11 of infusion sheath 12. As was discussed in respect to FIG. 3, although holes 14 of sheath 12 are not shown in this view, it should be understood that the holes are present and they are configured and spaced as provided in connection with the description of FIG. 1. Catheter hub 44 can be gripped by a user to advance and manipulate catheter 42 into and through sheath 12. FIG. 5A is an enlarged sectional view depicting catheter 42 located in sheath 12 and further depicts space 15a created between outer wall surface 43 of catheter 42 and innerwall surface 25 of sheath 12. Catheter 42 is sized and configured such that it is smaller in cross section than lumen 11 to create space 15a for the passage of fluid around outer wall surface 43. As with the use of the aforementioned dilator, it is the space 15a which receives fluid F directed through the sidearm 18 and allows, in this embodiment, passage of at least a portion of the fluid through sheath holes 14 (not shown in this view) for delivery of the fluid to the environment surrounding sheath 12. FIG. 5B is an enlarged sectional view depicting distal end portion 12a of sheath 12 and showing catheter 42 passing through distal end 12b of sheath 12. There is a clearance or space 15b between distal end 12b and catheter wall 43. Thus, while some of the introduced fluid F will exit side holes 14, fluid will also exit through distal end 12b.

Turning next to FIG. 6., there is shown yet another embodiment 10b of the invention. Here there is depicted a device like that discussed in respect to FIG. 3 but employing another modified dilator 46. Dilator 46 includes a lumen 48, a closed distal end 50 and one or more holes 52 disposed along the dilator wall 54. The dilator also includes a hub 30b which is like hub 30, 30a previously mentioned. In this embodiment, fluid F' is typically delivered into lumen 48 at hub 30b for passage through lumen 48 and out holes 52 for delivery to side holes 14 (not shown) of sheath 12. If desired, one could deliver fluid through stopcock 16 as disclosed in respect to embodiments of devices 10 and 10a.

FIG. 6A is an enlarged sectional view depicting dilator 46 located in sheath 12 and further depicts space 15c created between outer wall surface 23b of dilator 46 and innerwall surface 25 of sheath 12. Dilator 46 is shown to be sized and configured such that it is smaller in cross section than lumen 11 to create space 15c for the passage of fluid around outer wall surface 23b. However, it should be understood that there need be no space created when fluid F' is delivered provided that dilator holes 52 are in fluid communication with sheath holes 14. Should it be desired to deliver fluid F as in the aforementioned embodiments, then a space would be required and, as with the use of the aforementioned embodiments, fluid F would be directed through the sidearm 18 for passage of the fluid through sheath holes 14 (not shown in this view) for delivery of the fluid to the environment surrounding sheath 12.

FIG. 6B is an enlarged sectional view depicting distal end portion 12a of sheath 12 and showing a dilator portion 24a much like enlarged dilator portion 24 discussed above. At distal end 12b, dilator 46 forms a seal 36a to create a fluid barrier at the distal end of the sheath. At the location of seal 36a, the diameter of dilator section 24b is sized to be at least equal to lumen 11 at the distal end 12b of sheath 12 and may be slightly larger to create the fluid barrier. FIG. 6C is an enlarged sectional view showing lumen 48 and closed distal end 50 of dilator 46. All introduced fluid, either F or F', will exit side holes 14.

Turning lastly to FIG. 7, there is shown yet another embodiment 10c of the invention. Here there is depicted a device like that discussed in respect to FIG. 3 but employing still another modified dilator 56. Dilator 56 includes a lumen 40a, an open distal end portion 32b, one or more additional lumens 58 disposed in dilator wall 60, and one or more holes 62 disposed along the dilator wall 60. The dilator also includes hubs 30c through which fluid F' and F'" might be delivered. In this embodiment, either fluid F' or F'" might be delivered into one or more lumens 58 for passage through lumen(s) 58 and out holes 62 for delivery to side holes 14 (not shown) of sheath 12. Additionally, if desired, one could deliver fluid through stopcock 16 as disclosed in respect to embodiments of devices 10 and 10a.

FIG. 7A is an enlarged cross sectional view depicting dilator 56 located in sheath 12 and further depicts dilator lumens 40a and 58, opening 62 and space 15d. FIG. 7B shows space 15d created between outer wall surface 23c of dilator 56 and innerwall surface 25 of sheath 12. Dilator 56 is shown to be sized and configured such that it is smaller in cross section than lumen 11 to create space 15d for the passage of fluid around outer wall surface 23c. However, it should be understood that there need be no space created when either fluid F' or F'" is delivered to lumen 58 provided that dilator holes 62 in wall 60 are in fluid communication with sheath holes 14. Should it be desired to deliver fluid F via stopcock 16 as in some of the aforementioned embodiments, then a space would be required and as with the use of the aforementioned embodiments fluid F is directed through the sidearm 18 for passage of the fluid through sheath holes 14 (not shown in this view) for delivery of the fluid to the environment surrounding sheath 12.

FIG. 7C is an enlarged sectional view depicting distal end portion 12a of sheath 12 and showing a dilator portion 24c much like enlarged dilator portion 24 discussed above. At distal end 12b, dilator 56 forms a seal 36b to create a fluid barrier at the distal end of the sheath. At the location of seal 36b, the diameter of dilator section 24c is sized to be at least equal to lumen 11 at the distal end 12b of sheath 12 and may be slightly larger to create the fluid barrier. In this view, lumen 58, opening 62 and space 15d are additionally illustrated. FIG. 7D is an enlarged sectional view provided to show the structural features of the distal end portion 32b of dilator 56 with lumens 40a, 58 and distal tip 34b. Substantially all introduced fluid, F, F' or F'", will exit side holes 14 (not shown).

As a non-limiting example of the principles of the invention in use, a dilator will be snapped into place in the sheath-dilator assembly and the assembly will be used to introduce the sheath into the vessel of a patient as per any standard procedure. At that time, if the physician desires to inject medication of any type, the dilator would be left in place. The medication would be injected through the stopcock attached to the sidearm of the sheath. With the dilator in place and a fluid seal established at the distal end of the sheath, this would allow all or substantially all of the medication to flow out the apertures in the sheath wall. When the sheath is introduced and the physician does not intend to take advantage of the primary feature of infusion mainly through the side holes, namely fluid delivery predominantly along the sheath wall, the dilator would be withdrawn. The sheath would then used as a conventional sheath and medication would flow primarily through the end of the sheath although some fluid would flow out the side holes. If at any time during the procedure the physician wishes to take advantage of the enhanced feature of fluid delivery along the sheath wall instead of substantially through the end of the sheath, he would use the infusion sheath feature, the dilator would be re-inserted, snapped into place, and medication injected as above. As an alternative, the physician may choose to infuse medication with a catheter in place (after the dilator had been previously removed and a catheter inserted). If this is the case, medication would be injected into the stopcock as noted above. A portion of the medication would flow out the side holes and a portion would likely flow out the end of the sheath.

What is claimed is:

1. A vascular device for infusion of fluids into a patient comprising a first elongated tubular member having a proximal end, a distal end, at least a first lumen extending therethrough and a first wall having an outer surface and extending between said proximal end and said distal end, a second tubular member having a second wall, said second wall having at least one longitudinally disposed groove there in, and being positioned within said lumen to define a space between said first wall and said second wall, said space being adapted to receive a fluid, said second tubular member being sized and configured to create a fluid seal proximate said distal end of said second tubular member, and one or more apertures disposed in said first wall between said proximal end and said distal end for providing fluid communication between said space and an environment surrounding said outer surface of said first wall, wherein fluid interceded into said space exits said device substantially only through said one or more apertures along a length of said outer surface of said first wall.

2. The device according to claim 1 wherein said one or more apertures are disposed circumferentially about said first wall.

3. The device according to claim 2 wherein said one or more apertures are disposed in a helical pattern.

4. The device according to claim 2 wherein said one or more apertures are disposed longitudinally along said first wall.

5. The device according to claim 1 wherein said one or more apertures have a diameter in a range of about 0.025 mm to about 0.600 mm.

6. The device according to claim 1 wherein said one or more apertures have a diameter of about 0.125 mm.

7. The device according to claim 1 wherein said one or more apertures are spaced from about 1 mm to about 200 mm apart.

8. The device according to claim 7 wherein said one or more apertures are spaced about 10 mm apart.

9. The device according to claim 1 wherein said first tubular member has a length in a range of from about 10 cm to about 25 cm.

10. The device according to claim 1 further including means for delivering said fluid to said space.

11. The device according to claim 1 wherein said second tubular member is a dilator.

12. The device according to claim 11 wherein said dilator comprises a first portion having a first diameter and a second diameter, with said first diameter being greater than said second diameter.

13. The device according to claim 12 wherein said first diameter at a first predetermined location has a diameter being at least equal to said lumen at said first predetermined location.

14. The device according to claim 12 wherein said diameter at a second predetermined location has a diameter being less than said lumen at said second predetermined location.

15. The device according to claim 11 wherein said dilator comprises a closed distal end and at least a second lumen therein communicating with said space, said second lumen being adapted to receive said fluid and delivering said fluid to said space.

16. The device according to claim 11 wherein said second wall of said dilator comprises at least a second lumen disposed in said second wall communicating with said space, said at least a second lumen being adapted to receive said fluid and delivering said fluid to said space.

17. A vascular device for infusion of fluids into a patient comprising a first elongated tubular member having a proximal end, a distal end and a lumen extending therethrough, a first wall extending between said proximal end and said distal end, with said first tubular member having a through opening at said distal end, a second tubular member having a second wall, said second wall having at least one longitudinally disposed groove there in, and being positioned within said lumen to define a space between said first wall and said second wall, said space being adapted to receive a fluid, with a portion of said second member extending through said opening at said distal end of said first tubular member, and one or more apertures disposed in said first wall between said proximal end and said distal end for providing fluid communication between said space and an environment external of said device, wherein a portion of said fluid introduced into said space exits said device through said one or more apertures along the length of said first wall.

18. The device according to claim 17 wherein said second tubular member is a catheter.

19. A vascular device for infusion of fluids into a patient comprising a first elongated tubular member having a proximal end, a distal end and a lumen extending therethrough, and a first wall having an outer surface and extending between said proximal end and said distal end, a second tubular member having a second wall, said second wall having at least one longitudinally disposed groove there in, and being positioned within said lumen to define a space between said first wall and said second wall, said space being adapted to receive a fluid, and one or more apertures disposed in said first wall between said proximal end and said distal end for providing fluid communication between said space and an environment surrounding said outer surface of said first wall, wherein fluid introduced into said space exits said device substantially only through said one or more apertures alone the length of said outer surface of said first wall.

20. The device according to claim 19 wherein said second tubular member is a dilator.

* * * * *